United States Patent
Zan

(10) Patent No.: US 12,128,253 B2
(45) Date of Patent: Oct. 29, 2024

(54) METHOD AND APPARATUS FOR POSITIONING PATIENT

(71) Applicant: OUR UNITED CORPORATION, Xi'an (CN)

(72) Inventor: Peng Zan, Xi'an (CN)

(73) Assignee: OUR UNITED CORPORATION, Xi'an (CN)

( * ) Notice: Subject to any disclaimer, the term of this patent is extended or adjusted under 35 U.S.C. 154(b) by 450 days.

(21) Appl. No.: 17/604,152

(22) PCT Filed: Apr. 14, 2020

(86) PCT No.: PCT/CN2020/084639
§ 371 (c)(1),
(2) Date: Oct. 15, 2021

(87) PCT Pub. No.: WO2020/211739
PCT Pub. Date: Oct. 22, 2020

(65) Prior Publication Data
US 2022/0193454 A1    Jun. 23, 2022

(30) Foreign Application Priority Data
Apr. 18, 2019   (CN) .......................... 201910313347.4

(51) Int. Cl.
*A61N 5/10* (2006.01)

(52) U.S. Cl.
CPC ................................. *A61N 5/1049* (2013.01)

(58) Field of Classification Search
CPC .. A61N 5/1049; A61N 5/1069; A61N 5/1048; A61N 5/103; A61B 6/04; A61B 6/469; A61B 6/0487
See application file for complete search history.

(56) References Cited

U.S. PATENT DOCUMENTS 4,481,657 A * 11/1984 Larsson ............... A61B 6/0464
                                                378/91
5,825,845 A * 10/1998 Blair ................... A61N 5/1049
                                                378/65
(Continued)

FOREIGN PATENT DOCUMENTS

CN      104491991 A      4/2015
CN      106621078 A      5/2017
(Continued)

OTHER PUBLICATIONS

International search report of PCT application No. PCT/CN2020/084639 issued on Jul. 15, 2020.
(Continued)

*Primary Examiner* — David A Vanore
(74) *Attorney, Agent, or Firm* — Knobbe, Martens, Olson & Bear, LLP

(57) ABSTRACT

Provided are a method and apparatus for positioning a patient. The method can include: acquiring a setup parameter of a patient in a positioning area, wherein the setup parameter includes an offset desired by the patient when a site to be treated of the patient is coincident with a virtual isocenter; and adjusting a position of the patient in a treatment room based on the setup parameter and a preset positional relationship between the virtual isocenter and an isocenter of a radiotherapy device, such that the site to be treated of the patient is coincident with the isocenter of the radiotherapy device.

18 Claims, 2 Drawing Sheets

(56) References Cited

U.S. PATENT DOCUMENTS

| | | | |
|---|---|---|---|
| 6,600,164 B1* | 7/2003 | Badura | A61N 5/1048 250/492.1 |
| 8,758,263 B1 | 6/2014 | Rahimian et al. | |
| 9,950,194 B2* | 4/2018 | Bouchet | A61N 5/1049 |
| 2004/0184583 A1* | 9/2004 | Nagamine | A61N 5/1049 378/209 |
| 2006/0063999 A1* | 3/2006 | Herron | A61N 5/1049 378/65 |
| 2006/0203958 A1* | 9/2006 | Nagamine | A61N 5/1049 378/20 |
| 2006/0215813 A1* | 9/2006 | Scherch | A61N 5/1049 378/65 |
| 2009/0171184 A1* | 7/2009 | Jenkins | G01R 33/3415 606/130 |
| 2015/0324967 A1* | 11/2015 | Newell | G06T 7/277 382/103 |
| 2018/0078785 A1* | 3/2018 | Ollila | A61N 5/1039 |
| 2018/0078789 A1* | 3/2018 | Ollila | A61N 5/1042 |
| 2018/0111007 A1* | 4/2018 | Gordon | A61N 5/1067 |
| 2020/0185079 A1* | 6/2020 | Yan | A61N 5/1075 |
| 2020/0376301 A1* | 12/2020 | Liu | A61N 5/1042 |
| 2021/0016110 A1* | 1/2021 | Gou | A61N 5/1049 |
| 2021/0077053 A1* | 3/2021 | Efrati | A61B 6/544 |
| 2021/0252309 A1* | 8/2021 | Yan | G06T 7/0012 |
| 2022/0193454 A1* | 6/2022 | Zan | A61N 5/1049 |

FOREIGN PATENT DOCUMENTS

| | | |
|---|---|---|
| CN | 106943678 A | 7/2017 |
| CN | 107823807 A | 3/2018 |
| CN | 108273199 A | 7/2018 |
| CN | 108635681 A | 10/2018 |
| CN | 108969912 A | 12/2018 |
| CN | 109078270 A | 12/2018 |
| CN | 109310878 A | 2/2019 |
| CN | 109453472 A | 3/2019 |
| JP | 2000288102 A | 10/2000 |
| JP | 2007289373 A | 11/2007 |
| JP | 2012148026 A | 8/2012 |
| JP | 2014171560 A | 9/2014 |
| WO | 2018112070 A1 | 6/2018 |

OTHER PUBLICATIONS

First office action of Chinese application No. 201910313347.4 issued on Feb. 20, 2021.

Second office action of Chinese application No. 201910313347.4 issued on Sep. 15, 2021.

* cited by examiner

METHOD AND APPARATUS FOR POSITIONING PATIENT

CROSS-REFERENCE TO RELATED APPLICATION

The application is a US national stage of international patent application No. PCT/CN2020/084639 filed on Apr. 14, 2020, which claims priority to Chinese Patent Application No. 201910313347.4, filed on Apr. 18, 2019 and titled "METHOD AND APPARATUS FOR POSITIONING PATIENT," each of which is incorporated herein by reference in its entirety.

TECHNICAL FIELD

The present disclosure relates to the field of radiotherapy systems, in particular to a method for positioning a patient.

BACKGROUND

The radiotherapy technique is currently one of the most important methods for the treatment of tumors, which irradiates a patient's lesion using rays to achieve a treatment purpose. In the course of the treatment, it is very important to accurately position a patient and ensure the consistency of a position of rays and the lesion.

SUMMARY

The present disclosure provides a method and apparatus for positioning a patient, and employs the following technical solutions.

Embodiments of the present disclosure provide a method for positioning a patient. The method includes:
  acquiring a setup parameter of a patient in a positioning area, wherein the setup parameter includes an offset that the patient needs to perform when a site to be treated of the patient is coincident with a virtual isocenter; and
  adjusting a position of the patient in a treatment room based on the setup parameter and a preset positional relationship between the virtual isocenter and an isocenter of a radiotherapy device, such that the site to be treated of the patient is coincident with the isocenter of the radiotherapy device.

In a possible embodiment, the virtual isocenter includes: a first virtual isocenter provided by a first positioning mechanism in the positioning area.

In a possible embodiment, acquiring the setup parameter of the patient in the positioning area includes:
  acquiring an offset of the first positioning mechanism in the positioning area, wherein the offset of the first positioning mechanism includes an offset by which the first positioning mechanism is moved such that the first virtual isocenter provided by the first positioning mechanism reaches the site to be treated of the patient; and
  generating the setup parameter of the patient located in the positioning area based on the offset of the first positioning mechanism in the positioning area.

In a possible embodiment, acquiring the setup parameter of the patient in the positioning area includes:
  acquiring an offset of the patient in the positioning area, wherein the offset of the patient in the positioning area includes an offset by which the site to be treated of the patient is moved to the first virtual isocenter; and
  generating the setup parameter of the patient located in the positioning area based on the offset of the patient in the positioning area.

In a possible embodiment, the virtual isocenter further includes: a second virtual isocenter provided by a second positioning mechanism in the treatment room, wherein
  a relative positional relationship between the second positioning mechanism and the treatment couch in the treatment room is consistent with a relative positional relationship between the first positioning mechanism and a pre-positioning couch in the positioning area.

In a possible embodiment, a pre-positioning couch configured to carry the patient is arranged in the positioning area; and a treatment couch configured to the patient is arranged in the treatment room, wherein a relative positional relationship between the isocenter of the radiotherapy device and the treatment couch is consistent with a relative positional relationship between the virtual isocenter and the pre-positioning couch; and
  correspondingly, adjusting the position of the patient in the treatment room includes:
  instructing to move the patient from the pre-positioning couch in the positioning area to the treatment couch in the treatment room, and instructing to secure the patient on the treatment couch, wherein a relative positional relationship between the patient in the treatment room and the treatment couch is consistent with a relative positional relationship between the patient in the positioning area and the pre-positioning couch; and
  adjusting the position of the treatment couch based on the setup parameter, such that the site to be treated of the patient is coincident with the isocenter of the radiotherapy device.

In a possible embodiment, a pre-positioning couch is arranged in the positioning area, wherein the pre-positioning couch includes a pre-positioning couch body and a movable couch board located on the pre-positioning couch body for carrying the patient; and a treatment couch body configured to carry the movable couch board is arranged in the treatment room, wherein a relative positional relationship between the isocenter of the radiotherapy device and the treatment couch body is consistent with a relative positional relationship between the virtual isocenter and the pre-positioning couch body; and
  correspondingly, adjusting the position of the patient in the treatment room includes:
  instructing to move the movable couch board carrying the patient to the treatment couch body in the treatment room, wherein a relative positional relationship between the movable couch board in the treatment room and the treatment couch body is consistent with a relative positional relationship between the movable couch board in the positioning area and the pre-positioning couch body; and
  adjusting the position of the movable couch board based on the setup parameter, such that the site to be treated of the patient is coincident with the isocenter of the radiotherapy device.

In a possible embodiment, a pre-positioning couch configured to carry the patient is arranged in the positioning area; and
  correspondingly, adjusting the position of the patient in the treatment room includes:
  instructing to move the pre-positioning couch from the positioning area to the treatment room as a treatment couch, wherein a relative positional relationship between the isocenter of the radiotherapy device and the treatment couch is consistent with a relative positional relationship between the virtual isocenter and the pre-positioning couch; and adjusting the position of the pre-positioning couch based on the setup parameter, such that the site to be treated of the patient is coincident with the isocenter of the radiotherapy device.

In a possible embodiment, in response to acquiring the setup parameter of the patient in the positioning area, the method further includes:

calibrating the setup parameter through an image guided system arranged in the positioning area, such that the site to be treated of the patient is coincident with the isocenter of the radiotherapy device.

In a possible embodiment, prior to acquiring the setup parameter of the patient in the positioning area, the method further includes:

verifying an identity of the patient.

In a possible embodiment, acquiring the setup parameter of the patient in the positioning area includes:

acquiring the setup parameter of the patient located in the positioning area; and correspondingly, in response to acquiring the setup parameter of the patient in the positioning area, the method further includes:

adjusting the position of the patient from the positioning area to a waiting area.

Embodiments of the present disclosure further provide an apparatus for positioning a patient. The apparatus includes a processor and a memory configured to store a program instruction therein, wherein the processor, when calling the program instruction from the memory, is caused to perform any of the above methods.

Embodiment of the present disclosure further provide a computer-readable storage medium. The computer-readable storage medium is configured to store a computer program therein, the computer program including a program instruction, which, when executed by a processor, causes the processor to perform any of the above methods.

BRIEF DESCRIPTION OF THE DRAWINGS

For clearer descriptions of the technical solutions according to the embodiments of the present disclosure, the following briefly introduces the accompanying drawings required for describing the embodiments. Apparently, the accompanying drawings in the following description only show some embodiments of the present disclosure, and for persons of ordinary skill in the art may still derive other drawings from these accompanying drawings without creative efforts.

Figure 1:
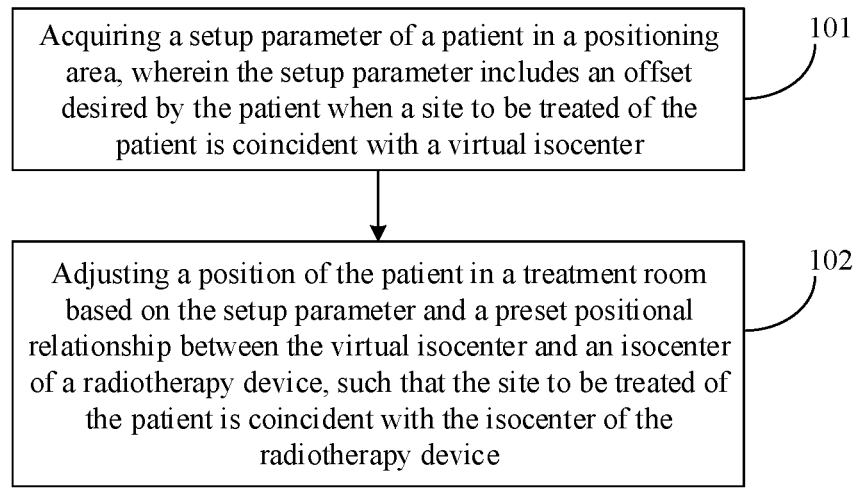
FIG. 1 is a flowchart of a method for positioning a patient according to an embodiment of the present application.

Reference numerals and denotations thereof:
A-laser lamp, and D-virtual isocenter.

DETAILED DESCRIPTION

The embodiments of the present application are described below with reference to the accompanying drawings.

In the related arts, a patient is positioned in the following ways: a therapist positions the patient who is lying on a treatment couch in a treatment room; and next, the treatment couch is driven to move the patient into a treatment area of a radiotherapy device, such that a target of the patient is coincident with an isocenter of the radiotherapy device for the treatment of the patient.

However, for the entire treatment process, actual treatment time is relatively short, whereas prior to the treatment, positioning the patient in the treatment room takes up more time, resulting in a decline in the utilization rate of the radiotherapy device.

As mentioned above, in the prior art, it takes a long time to position a patient in a treatment room, and a radiation therapy device (hereinafter referred to as a radiotherapy device) in the treatment room is vacant during the time period occupied by the positioning, and cannot be used effectively, resulting in a decline in its utilization rate. In order to solve this technical problem, an embodiment of the present disclosure provides a method for positioning a patient, which can effectively increase the utilization rate of a radiotherapy device.

FIG. 1 is a flowchart of a method for positioning a patient according to an embodiment of the present disclosure. The method for positioning the patient includes the following steps.

In step 101, a setup parameter of the patient in a positioning area is acquired, wherein the setup parameter includes an offset desired the patient when a site to be treated of the patient is coincident with a virtual isocenter.

In step 102, a position of the patient in a treatment room is adjusted based on the setup parameter and a preset positional relationship between the virtual isocenter and an isocenter of a radiotherapy device, such that the site to be treated of the patient is coincident with the isocenter of the radiotherapy device.

In the method for positioning the patient according to the embodiment of the present disclosure, by acquiring the setup parameter of the patient in the positioning area, it is ensured that the site to be treated (such as each target) of the patient in the positioning area is coincident with the virtual isocenter. Since the setup parameter indicates the offset desired by the patient when the site to be treated of the patient is coincident with the virtual isocenter in the positioning area, on the premise of the determination of the positional relationship between the virtual isocenter and the isocenter of the radiotherapy device, the position of the patient can be adjusted based on the setup parameter after the patient enters the treatment room, such that the site to be treated of the patient is coincident with the isocenter of the radiotherapy device. According to the method for positioning the patient according to the embodiment of the present disclosure, based on the above steps, the patient is subject to pre-positioning in the positioning area before entering the treatment room; and based on this pre-positioning, the patient is positioned rapidly and accurately after entering the treatment room. Therefore, the positioning time of the patient in the treatment room is significantly reduced, and hence the utilization rate of the radiotherapy device is improved.

In the embodiment of the present disclosure, the positioning area is configured to provide a pre-positioning place for a patient to be treated, before the patient enters the treatment room where the radiotherapy device is placed for formal treatment. It may be understood that the positioning area involved in the embodiment of the present disclosure is an area which is different from a treatment room area where the radiotherapy device is placed.

The virtual isocenter includes: a first virtual isocenter provided by a first positioning mechanism in the positioning area.

The positioning mechanism is an apparatus configured to correct a body position before radiotherapy. In the embodiment of the present disclosure, the positioning mechanism is configured to provide a virtual isocenter so as to ensure the accuracy of the virtual isocenter.

In the embodiment of the present application, the positioning way of the positioning mechanism includes but is not limited to: laser, visible light, infrared and radioactive imaging, such as cone beam CT (CBCT), or the like.

Figure 2:
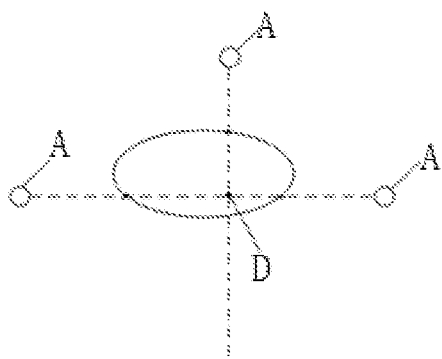
FIG. 2 is a schematic diagram of an exemplary positioning mechanism forming a virtual isocenter.

Taking the positioning mechanism being a laser positioning mechanism as an example, as shown in FIG. 2, the positioning mechanism may include: three laser lights A (for example, the three laser lights A may be respectively located on three walls of a pre-positioning room), wherein three laser beams emitted from the three laser lights A intersect at one point, which is the virtual isocenter D. A positional relationship between the virtual isocenter D and the isocenter of the radiotherapy device in the treatment room is determined. Optionally, a positional relationship between the virtual isocenter D and a specific object in the positioning area, and a positional relationship between the isocenter of the radiotherapy device and the specific object in the treatment room may be adjusted and the two positional relationships may be adjusted to be consistent.

When the first positioning mechanism provides a first virtual isocenter, the setup parameter of the patient located in the positioning area can be acquired in different ways, which are illustrated in the following examples.

In an example, step 101 includes:
acquiring an offset of the first positioning mechanism in the positioning area, wherein the offset of the first positioning mechanism includes an offset by which the first positioning mechanism is moved such that the first virtual isocenter provided by the first positioning mechanism reaches the site to be treated of the patient; and
generating the setup parameter of the patient located in the positioning area based on the offset of the first positioning mechanism in the positioning area.

In this example, the setup parameter is acquired by moving the first positioning mechanism, wherein the offset generated by the first positioning mechanism during the movement includes the moving distance thereof in a three-dimensional direction. In order to acquire the setup parameter more intuitively, the setup parameter of the patient in the positioning area is generated by converting the offset of the first positioning mechanism in the positioning area, i.e., the offset of the patient, e.g., the moving distance in the three-dimensional direction.

In another example, step 101 includes:
acquiring an offset of the patient in the positioning area, wherein the offset of the patient in the positioning area includes an offset by which the site to be treated of the patient is moved to the first virtual isocenter; and
generating the setup parameter of the patient located in the positioning area based on the offset of the patient in the positioning area.

In this example, the offset of the patient in the positioning area, i.e., the moving distance in the three-dimensional direction, is acquired by moving the patient, which may not be converted and may generate setup parameter directly.

Optionally, in the embodiment of the present disclosure, the virtual isocenter further includes: a second virtual isocenter provided by a second positioning mechanism in the treatment room, wherein a relative positional relationship between the second positioning mechanism and the treatment couch in the treatment room is consistent with a relative positional relationship between the first positioning mechanism and a pre-positioning couch in the positioning area.

By providing the second virtual isocenter in the treatment room and making the relative positional relationship between the second positioning mechanism and the treatment couch in the treatment room consistent with the relative positional relationship between the first positioning mechanism and the pre-positioning couch in the positioning area, the site to be treated of the patient is in fast coincident with the second virtual isocenter when the setup parameter acquired by position presetting of the patient in the positioning area can be directly used for the positioning of the patient in the treatment room. In addition, the positional relationship between the second virtual isocenter and the isocenter of the radiotherapy device is also determined. The position of the patient is adjusted based on the preset positional relationship between the second virtual isocenter and the isocenter of the radiotherapy device, so as to achieve the purpose of making the isocenter of the site to be treated of the patient coincide with the isocenter of the radiotherapy device, thereby realizing the rapid positioning of the patient.

The virtual isocenter may also be a preset point. How to set the virtual isocenter is not limited here.

After acquiring the setup parameter and the preset positional relationship between the virtual isocenter and the isocenter of the radiotherapy device, the position of the patient in the treatment room may be adjusted in different ways based on different scenarios (that is, scenarios where the positional relationships between the virtual isocenter and the isocenter of the radiotherapy device are different). The followings are respectively described in combination with specific scenarios.

In a possible example, a pre-positioning couch configured to carry the patient is arranged in the positioning area; and a treatment couch configured to carry the patient is arranged in the treatment room, wherein a relative positional relationship between the isocenter of the radiotherapy device and the treatment couch is consistent with a relative positional relationship between the virtual isocenter and the pre-positioning couch.

Based on the above scenario, step 102 includes:
instructing to move the patient from the pre-positioning couch in the positioning area to the treatment couch in the treatment room, and instructing to secure the patient on the treatment couch, wherein a relative positional relationship between the patient in the treatment room and the treatment couch is consistent with a relative positional relationship between the patient in the positioning area and the pre-positioning couch.

The position of the treatment couch is adjusted based on the setup parameter, such that the site to be treated of the patient is coincident with the isocenter of the radiotherapy device.

Since the relative positional relationship between the isocenter point of the radiotherapy device and the treatment couch is consistent with the positional relationship between the virtual isocenter and the pre-positioning couch, this means that the setup parameter not only indicates the offset desired for moving the patient such that the site to be treated of the patient is coincident with the virtual isocenter, but also indicates the offset desired for moving the patient such that the site to be treated of the patient is coincident with the isocenter of the radiotherapy device. In this case, the position of the patient is adjusted by adjusting the position of the treatment couch in the treatment room based on the setup parameter, so as to achieve the purpose that the site to be treated of the patient is coincident with the isocenter of the radiotherapy device.

The position of the treatment couch in the treatment room may be adjusted, such that a relative positional relationship between the isocenter of the radiotherapy device and the treatment couch is consistent with a relative positional relationship between the virtual isocenter and the pre-positioning couch.

In another possible example, the pre-positioning couch is arranged in the positioning area. The pre-positioning couch includes a pre-positioning couch body, and a movable couch board located on the pre-positioning couch body for carrying the patient. A treatment couch body configured to support the movable couch board is arranged in the treatment room. A relative positional relationship between the isocenter of the radiotherapy device and the treatment couch body is consistent with a relative positional relationship between the virtual isocenter and the pre-positioning couch body.

Based on the above scenario, step 102 includes:
  instructing to move the movable couch board carrying the patient to the treatment couch body in the treatment room, wherein a relative positional relationship between the movable couch board in the treatment room and the treatment couch body is consistent with a relative positional relationship between the movable couch board in the positioning area and the pre-positioning couch body; and
  adjusting the position of the movable couch board based on the setup parameter, such that the site to be treated of the patient is coincident with the isocenter of the radiotherapy device.

In this example, since the relative positional relationship between the isocenter point of the radiotherapy device and the treatment couch body is consistent with the relative positional relationship between the virtual isocenter and the pre-positioning couch body, it is also meant that the setup parameter not only indicates the offset desired by the patient when the site to be treated of the patient is coincident with the virtual isocenter, but also indicates the offset desired by the patient when the site to be treated of the patient is coincident with the isocenter of the radiotherapy device. In this case, the position of the patient may be adjusted by adjusting the position of the movable couch board on the treatment couch body based on the setup parameter, so as to achieve the purpose that the site to be treated of the patient is coincident with the isocenter of the radiotherapy device.

The position of the treatment couch body in the treatment room may be adjusted, such that the relative positional relationship between the isocenter of the radiotherapy device and the treatment couch is coincident with the relative positional relationship between the virtual isocenter and the pre-positioning couch.

In yet other possible example, a pre-positioning couch configured to carry the patient is arranged in the positioning area.

Based on the above scenario, step 102 includes:
  instructing to move the pre-positioning couch in the positioning area to the treatment room as the treatment couch, wherein a relative positional relationship between the isocenter of the radiotherapy device and the treatment couch is consistent with a relative positional relationship between the virtual isocenter and the pre-positioning couch.

The position of the pre-positioning couch (i.e., the treatment couch) may be adjusted based on the setup parameter, such that the site to be treated of the patient is coincident with the isocenter of the radiotherapy device.

In this example, since the pre-positioning couch is arranged only in the positioning area, and according to push the pre-positioning couch into the treatment room as a treatment couch and adjust its position, the relative positional relationship between the isocenter of the radiotherapy device and the treatment couch is consistent with the relative positional relationship between the virtual isocenter and the pre-positioning couch. In this case, the position of the patient is adjusted by adjusting the position of the treatment couch in the treatment room based on the setup parameter, so as to achieve the purpose that the site to be treated of the patient is coincident with the isocenter of the radiotherapy device.

The positioning area and the treatment room may be arranged on both sides of a wall, and there is a door on the partition wall between the positioning area and the treatment room. When the door is opened, it allows the patient, the movable couch or the pre-positioning couch to pass through.

Optionally, in order to calibrate the position of the patient and improve the positioning accuracy of the patient, the method provided by the embodiment of the present disclosure further includes: calibrating the setup parameter based on an image guided system arranged in the positioning area, such that the site to be treated of the patient is coincident with the isocenter of the radiotherapy device.

Through the image guided system, a positional error between the site to be treated of the patient and the virtual isocenter may be determined; and the setup parameter may be calibrated based on the positional error, so as to ensure that the site to be treated of the patient accurately is coincident with the isocenter of the radiotherapy device.

In an exemplary embodiment, a bulb tube and a detector which are opposite to each other are installed in the positioning area. After the positioning mechanism is used to complete the positioning, the image guided system is used to image the site to be treated of the patient. The acquired image of the site to be treated of the patient is registered with a CT image before treatment, to acquire a positional error (also referred to as a positional difference) between the site to be treated of the patient and the virtual isocenter. This positional error is recorded, and then after the patient enters the treatment room, the previously acquired setup parameter is calibrated based on the positional error, so as to position the patient accurately.

The radiotherapy device in the treatment room may also be equipped with an image guided system.

Optionally, prior to acquiring the setup parameter of the patient located in the positioning area, the method provided by the embodiment of the present disclosure further includes: verifying an identity of the patient so as to ensure that the identity of the patient being treated is correct and that a subject of treatment is correct.

The ways to verify the identity of the patient include but are not limited to: verifying a barcode or two-dimensional code with patient's identity information, verifying a patient's fingerprint, verifying a patient's facial image, and the like.

After the patient completes the position presetting in the positioning area, if other patient is being treated in the treatment room, a waiting area may also be arranged in the positioning area. In this case, said acquiring the setup parameter of the patient located in the positioning area includes: acquiring the setup parameter of the patient located in the positioning area.

Correspondingly, the method, after acquiring the setup parameter of the patient in the positioning area, further includes: adjusting the position of the patient from the positioning area to the waiting area.

It can be seen that before positioning, the patient subjected to position presetting is allowed to wait in the waiting area, which facilitates the position presetting of the next patient in the positioning area at the same time.

In order to relieve the nervousness of patients, decompressing items configured to relieve the patient's emotions are provided in the waiting area, such that the patients' emotions are relieved by the decompressing items in the waiting area. The decompressing items include, but are not limited to: a playback device configured to play videos or music, books, dolls, etc.

Taking a playback device as an example, the patient can independently select the playable videos or music.

Figure 3:
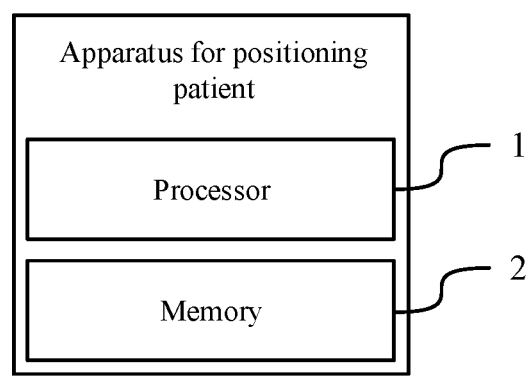
FIG. 3 is a structural block diagram of an apparatus for positioning a patient according to an embodiment of the present disclosure.

FIG. 3 is a structural block diagram of an apparatus for positioning a patient according to an embodiment of the present disclosure. As shown in FIG. 3, the apparatus for positioning the patient includes a processor 1 and a memory 2, wherein the memory 2 stores a program instruction therein, and the processor 1 is configured to call the program instruction in the memory 2 so as to execute any of the above methods for positioning the patient.

The processor 1 may include a central processing unit (CPU, single-core or multi-core), a graphics processing unit (GPU), a microprocessor, an application-specific integrated circuit (ASIC), a digital signal processor (DSP), a digital signal processing device (DSPD), a programmable logic device (PLD), a field programmable gate array (FPGA), a controller, a microcontroller, or a plurality of integrated circuits configured to control program execution.

The memory 2 may include, but be not limited to: a read-only memory (ROM), or other types of static storage devices that can store static information and instructions, a random-access memory (RAM) or other types of dynamic storage devices that can store information and instructions, or may include an electrically erasable programmable read-only memory (EEPROM), a compact disc read-only memory (CD-ROM) or other optical disc storage, optical disk storage (including a compact disk, a laser disk, an optical disk, a digital general disk, a Blu-ray disk, and the like), a magnetic disc storage medium or other magnetic storage devices, or any other medium which can be configured to carry or store desired program codes in the form of instructions or data structures, and can be accessed by a computer. The memory can be arranged independently or integrated with the processor.

In a specific implementation, as an embodiment, the processor 1 may include one or more CPUs. In a specific implementation, as an embodiment, the apparatus for positioning the patient may include a plurality of processors. Each of these processors may be a single-CPU processor or a multi-CPU processor. The processor here may refer to one or more devices, circuits, and/or processing cores configured to process data (for example, computer program instructions).

The above-mentioned apparatus for positioning the patient may include a general-purpose computer device or a special-purpose computer device. In a specific implementation, the computer device may be a desktop computer, a portable computer, a network server, a personal digital assistant (PDA), a mobile phone, a tablet computer, a wireless terminal device, a communication device, an embedded device, or a device with a similar structure.

An embodiment of the present disclosure further provides a computer storage medium configured to store a computer program used for any of the above methods for positioning the patient, the computer program including a program instruction. Any of the above methods for positioning the patient according to the embodiments of the present disclosure may be implemented by executing the stored program.

It should be understood by a person skilled in the art that the embodiments of the present disclosure may be provided as methods, apparatuses (devices) or computer program products. Therefore, the present disclosure may adopt the form of an entirely hardware embodiments, or an entirely software embodiments, or an embodiments including both software and hardware. Furthermore, the present disclosure may adopt forms of computer program products executed on one or more computer usable storage media (including but not being limited to a disk storage, a CD-ROM, an optical storage, and the like) containing computer usable program codes. The computer program may be stored/distributed in a suitable medium and provided with other hardware or as a part of the hardware, or may be distributed in other forms, such as through the Internet or other wired or wireless telecommunication systems.

The present disclosure is described with reference to the flowcharts and/or block diagrams of the method, the apparatus (device) and the computer program product according to the embodiments of the present disclosure. It should be understood that each process and/or block in the flowcharts and/or block diagrams, and combinations of processes and/or blocks in the flowcharts and/or block diagrams, may be realized by computer program instructions. These computer program instructions may be provided to a generate-purpose computer, a special-purpose computer, an embedded processor, or processors of other programmable data processing devices, to create a machine, such that an apparatus for realizing functions designated in one or more processes in the flowcharts and/or in one or more blocks in the block diagrams, may be created by instructions executed by a computer or processors of other programmable data processing devices.

These computer program instructions may further be stored in a computer readable storage that can boot a computer or other programmable data processing devices to work in a specific way, such that a manufactured goods including an instruction device may be created by the instructions stored in the said computer readable storage, and the said instruction device realizes the functions designated in one or more processes in the flowcharts and/or in one or more blocks in the block diagrams.

These computer program instructions may further be loaded into a computer or other programmable data processing devices, such that a series of operating steps may be executed on the computer or other programmable data processing devices, so as to generate processes realized by the computer, such that steps for realizing the functions designated in one or more processes in the flowcharts and/or in one or more blocks in the block diagrams may be provided by the instructions executed on the computer or other programmable data processing devices.

The above description is only for the convenience of a person skilled in the art to understand the technical solutions of the present disclosure, and it is not intended to limit the present disclosure. Thus, any modification, equivalent replacement, improvement and so on made within the spirit and principle of the present disclosure shall be encompassed by the protection scope of the present disclosure.

What is claimed is:

1. A method for positioning a patient, comprising:
acquiring a setup parameter of a patient in a positioning area, wherein the setup parameter comprises an offset desired by the patient when a site to be treated of the patient is coincident with a virtual isocentere; and
adjusting a position of the patient in a treatment room based on the setup parameter and a preset positional relationship between the virtual isocenter and an isocenter of a radiotherapy device, such that the site to be treated of the patient is coincident with the isocenter of the radiotherapy device.

2. The method according to claim 1, wherein the virtual isocenter comprises: a first virtual isocenter provided by a first positioning mechanism in the positioning area.

3. The method according to claim 2, wherein acquiring the setup parameter of the patient in the positioning area comprises:
acquiring an offset of the first positioning mechanism in the positioning area, wherein the offset of the first positioning mechanism comprises an offset by which the first positioning mechanism is moved such that the first virtual isocenter provided by the first positioning mechanism reaches the site to be treated of the patient; and
generating the setup parameter of the patient located in the positioning area based on the offset of the first positioning mechanism in the positioning area.

4. The method according to claim 2, wherein acquiring the setup parameter of the patient in the positioning area comprises:
acquiring an offset of the patient in the positioning area, wherein the offset of the patient in the positioning area comprises an offset by which the site to be treated of the patient is moved to the first virtual isocenter; and
generating the setup parameter of the patient located in the positioning area based on the offset of the patient in the positioning area.

5. The method according to claim 2, wherein the virtual isocenter further comprises: a second virtual isocenter provided by a second positioning mechanism in the treatment room; wherein
a relative positional relationship between the second positioning mechanism and a treatment couch in the treatment room is consistent with a relative positional relationship between the first positioning mechanism and a pre-positioning couch in the positioning area.

6. The method according to claim 1, wherein a pre-positioning couch configured to carry the patient is arranged in the positioning area; and the treatment couch configured to carry the patient is arranged in the treatment room, wherein a relative positional relationship between the isocenter of the radiotherapy device and the treatment couch is consistent with a relative positional relationship between the virtual isocenter and the pre-positioning couch; and
adjusting the position of the patient in the treatment room comprises:
instructing to move the patient from the pre-positioning couch in the positioning area to the treatment couch in the treatment room, and instructing to fix the patient on the treatment couch, wherein a relative positional relationship between the patient in the treatment room and the treatment couch is consistent with a relative positional relationship between the patient in the positioning area and the pre-positioning couch; and
adjusting the position of the treatment couch based on the setup parameter, such that the site to be treated of the patient is coincident with the isocenter of the radiotherapy device.

7. The method according to claim 1, wherein a pre-positioning couch is arranged in the positioning area, the pre-positioning couch comprising: a pre-positioning couch body and a movable couch board located on the pre-positioning couch body for carrying the patient; and a treatment couch body configured to support the movable couch board is arranged in the treatment room; wherein a relative positional relationship between the isocenter of the radiotherapy device and the treatment couch body is consistent with a relative positional relationship between the virtual isocenter and the pre-positioning couch body; and
adjusting the position of the patient in the treatment room comprises:
instructing to move the movable couch board carrying the patient to the treatment couch body in the treatment room, wherein a relative positional relationship between the movable couch board in the treatment room and the treatment couch body is coincident with a relative positional relationship between the movable couch board in the positioning area and the pre-positioning couch body; and
adjusting the position of the movable couch board based on the setup parameter, such that the site to be treated of the patient is coincident with the isocenter of the radiotherapy device.

8. The method according to claim 1, wherein a pre-positioning couch configured to carry the patient is arranged in the positioning area; and
adjusting the position of the patient in the treatment room comprises:
instructing to move the pre-positioning couch from the positioning area to the treatment room as a treatment couch; wherein a relative positional relationship between the isocenter of the radiotherapy device and the treatment couch is consistent with a relative positional relationship between the virtual isocenter and the pre-positioning couch; and
adjusting the position of the pre-positioning couch based on the setup parameter, such that the site to be treated of the patient is coincident with the isocenter of the radiotherapy device.

9. The method according to claim 1, wherein in response to acquiring the setup parameter of the patient in the positioning area, the method further comprises:
calibrating the setup parameter by an image guided system arranged in the positioning area, such that the site to be treated of the patient is coincident with the isocenter of the radiotherapy device.

10. The method according to claim 1, wherein acquiring the setup parameter of the patient in the positioning area comprises:
acquiring the setup parameter of the patient located in the positioning area; and
in response to acquiring the setup parameter of the patient in the positioning area, the method further comprises:
adjusting the position of the patient from the positioning area to a waiting area.

11. An apparatus for positioning a patient, comprising a processor and a memory storing instructions, wherein the processor, when executing the instructions stored the memory, is caused to perform a method for positioning a patient, wherein the method comprises:

acquiring a setup parameter of a patient in a positioning area, wherein the setup parameter comprises an offset desired by the patient when a site to be treated of the patient is coincident with a virtual isocenter; and adjusting a position of the patient in a treatment room based on the setup parameter and a preset positional relationship between the virtual isocenter and an isocenter of a radiotherapy device, such that the site to be treated of the patient is coincident with the isocenter of the radiotherapy device.

12. The apparatus according to claim 11, wherein the virtual isocenter comprises: a first virtual isocenter provided by a first positioning mechanism in the positioning area.

13. The apparatus according to claim 11, wherein a pre-positioning couch configured to carry the patient is arranged in the positioning area; and the treatment couch configured to carry the patient is arranged in the treatment room, wherein a relative positional relationship between the isocenter of the radiotherapy device and the treatment couch is consistent with a relative positional relationship between the virtual isocenter and the pre-positioning couch; and adjusting the position of the patient in the treatment room comprises:

instructing to move the patient from the pre-positioning couch in the positioning area to the treatment couch in the treatment room, and instructing to fix the patient on the treatment couch, wherein a relative positional relationship between the patient in the treatment room and the treatment couch is consistent with a relative positional relationship between the patient in the positioning area and the pre-positioning couch; and adjusting the position of the treatment couch based on the setup parameter, such that the site to be treated of the patient is coincident with the isocenter of the radiotherapy device.

14. The apparatus according to claim 11, wherein a pre-positioning couch is arranged in the positioning area, the pre-positioning couch comprising: a pre-positioning couch body and a movable couch board located on the pre-positioning couch body for carrying the patient; and a treatment couch body configured to support the movable couch board is arranged in the treatment room; wherein a relative positional relationship between the isocenter of the radiotherapy device and the treatment couch body is consistent with a relative positional relationship between the virtual isocenter and the pre-positioning couch body; and adjusting the position of the patient in the treatment room comprises:

instructing to move the movable couch board carrying the patient to the treatment couch body in the treatment room, wherein a relative positional relationship between the movable couch board in the treatment room and the treatment couch body is coincident with a relative positional relationship between the movable couch board in the positioning area and the pre-positioning couch body; and adjusting the position of the movable couch board based on the setup parameter, such that the site to be treated of the patient is coincident with the isocenter of the radiotherapy device.

15. The apparatus according to claim 11, wherein a pre-positioning couch configured to carry the patient is arranged in the positioning area; and adjusting the position of the patient in the treatment room comprises:

instructing to move the pre-positioning couch from the positioning area to the treatment room as a treatment couch; wherein a relative positional relationship between the isocenter of the radiotherapy device and the treatment couch is consistent with a relative positional relationship between the virtual isocenter and the pre-positioning couch; and adjusting the position of the pre-positioning couch based on the setup parameter, such that the site to be treated of the patient is coincident with the isocenter of the radiotherapy device.

16. The apparatus according to claim 11, wherein in response to acquiring the setup parameter of the patient in the positioning area, the method further comprises:

calibrating the setup parameter by an image guided system arranged in the positioning area, such that the site to be treated of the patient is coincident with the isocenter of the radiotherapy device.

17. The apparatus according to claim 11, wherein acquiring the setup parameter of the patient in the positioning area comprises:

acquiring the setup parameter of the patient located in the positioning area; and in response to acquiring the setup parameter of the patient in the positioning area, the method further comprises:

adjusting the position of the patient from the positioning area to a waiting area.

18. A non-transitory computer-readable storage medium storing a computer program, which, when executed by a processor, causes the processor to perform a method for positioning a patient, wherein the method comprises:

acquiring a setup parameter of a patient in a positioning area, wherein the setup parameter comprises an offset desired by the patient when a site to be treated of the patient is coincident with a virtual isocenter; and adjusting a position of the patient in a treatment room based on the setup parameter and a preset positional relationship between the virtual isocenter and an isocenter of a radiotherapy device, such that the site to be treated of the patient is coincident with the isocenter of the radiotherapy device.

* * * * *